United States Patent [19]

Lauffer et al.

[11] Patent Number: 5,318,978

[45] Date of Patent: Jun. 7, 1994

[54] AZABICYCLO OXIME AND AMINE CHOLINERGIC AGENTS AND METHODS OF TREATMENT

[75] Inventors: David J. Lauffer, Saline; Haile Tecle, Ypsilanti, both of Mich.

[73] Assignee: Warner-Lambert Company, Morris Plains, N.J.

[21] Appl. No.: 830

[22] Filed: Jan. 5, 1993

Related U.S. Application Data

[63] Continuation of Ser. No. 777,820, Oct. 15, 1991, abandoned.

[51] Int. Cl.$^5$ ............... C07D 471/08; A61K 31/435
[52] U.S. Cl. .................... 514/299; 546/112
[58] Field of Search .................... 546/112; 514/299

[56] References Cited

FOREIGN PATENT DOCUMENTS

| 0226267 | 6/1987 | European Pat. Off. |
| 287356 | 10/1988 | European Pat. Off. |
| 0338723 | 4/1989 | European Pat. Off. |
| 0363085 | 9/1989 | European Pat. Off. |
| 0414394 | 8/1990 | European Pat. Off. |

*Primary Examiner*—Marianne M. Cintins
*Assistant Examiner*—Catherine S. Kilby Scalzo
*Attorney, Agent, or Firm*—Michael J. Atkins

[57]. ABSTRACT

Pharmaceutically useful nitrogen containing cyclic oxime and amine substituted compounds of the formulas I to XVI are disclosed (See specification for definitions of the substituents). Specifically, the compounds are 1-azabicyclo [3.2.1] oximes, 1-azabicyclo [3.3.1] oximes, 1-aza-4-oxobicyclo [3.3.1] oximes, 1-aza-4-oxobicyclo [3.2.1] oximes, and the corresponding amines wherein the heterocyclic ring contains 7 or 8 carbon atoms

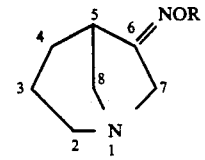

I

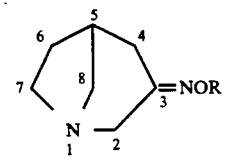

II

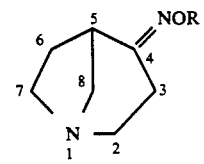

III

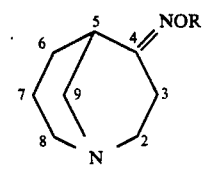

IV

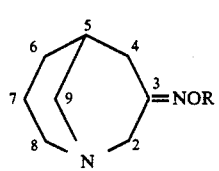

V

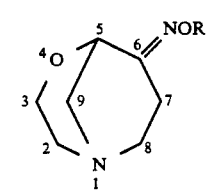

VI (Abstract continued on next page.)

-continued
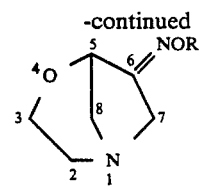  VII
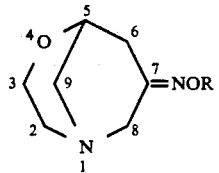  VIII
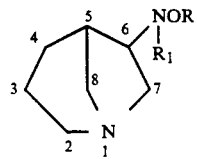  IX
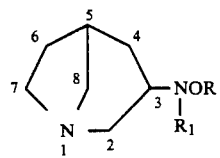  X
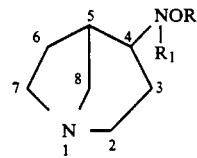  XI
-continued
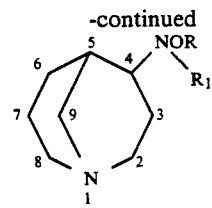  XII
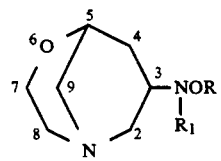  XIII
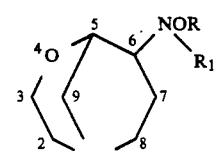  XIV
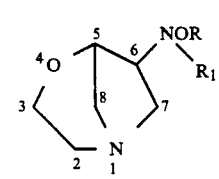  XV
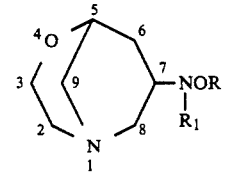  XVI
12 Claims, No Drawings

AZABICYCLO OXIME AND AMINE CHOLINERGIC AGENTS AND METHODS OF TREATMENT

This application is a file wrapper continuation of Ser. No. 07/777,820 filed Oct. 15, 1991 now abandoned.

FIELD OF INVENTION

The present invention is a class of oximes and amines which are muscarinic agonists, rendering them useful as pharmaceutical agents. More specifically, the compounds are azabicyclic oximes and amines.

BACKGROUND

Disorders of cognition are generally characterized by symptoms of forgetfulness, confusion, memory loss, attentional deficits, and/or, in some cases, affective disturbances. These symptoms may arise as a result of the general aging process and/or from organic brain disease, cerebrovascular disease, head injury, or developmental or genetic defects.

The general decrease in cognitive function which accompanies the aging process is well accepted. The same phenomenon has been observed and documented in many lower mammals, including those routinely employed in pharmacological testing programs for screening and predicting usefulness for particular drugs in higher animals, including humans.

Although disorders of cognition often accompany the general aging process, presenile and senile primary degenerative dementia are the most common accepted causes of mental deterioration in the elderly. It has been estimated that at least ten percent of persons over 60 years of age will eventually suffer severe mental deterioration. A much larger number will experience cognitive decline of sufficient severity to impede their activities.

Many of the symptoms of cognitive disorders, especially impaired memory, are associated with decreased acetylcholine synthesis and the impairment of cholinoreceptive neurons. In the hippocampus and cerebral cortex of patients suffering from primary degenerative dementia, for example, the level of the enzyme choline acetyltransferase (CAT) can be reduced by as much as 90%. (See Davies, et al, *The Lancet,* 1976 (Vol. 2):1403; Perry, et al, *J. Neurol. Sci.,* 34:247-265 (1977); and White, et al, *The Lancet,* 1977 (Vol. 1):668-670).

Since CAT catalyzes the synthesis of acetylcholine from its precursors choline and acetyl coenzyme A, the loss of CAT reflects the loss of cholinergic, or acetylcholine-releasing, nerve endings in the hippocampus and cerebral cortex. There is abundant evidence that cholinergic terminals in the hippocampus are critically important for memory formation.

The cholinergic hypothesis suggests that drugs which restore acetylcholine levels or which mimic the action of acetylcholine (i.e., are cholinomimetic) are effective in correcting this deficit in neurotransmitter chemical and provide treatment of the memory impairment symptom of cerebral insufficiency. Considerable biochemical, pharmacological, and electrophysiological evidence supports the hypothesis that deficits in the cholinergic system underlie geriatric cognitive dysfunction. (See C. Peterson and G. E. Gibson, *Neurobiol. Aging,* 4:25-30 (1983)). Aged humans and nonhuman primates with decreased cognition show improved memory when they are treated, for example, with acetylcholinesterase inhibitors such as physostigmine. These agents increase the available supply of synaptic acetylcholine by inhibiting its hydrolysis.

Aminopyridines such as 3,4-diaminopyridine ameliorate age-related cognitive deficits by increasing the release of acetylcholine from presynaptic nerve terminals, thus increasing synaptic acetylcholine. (See H. P. Davis, et al, *Exp. Aging Res.,* 9:211-214 (1983)).

It has been known for some time that the natural alkaloid, muscarine, has the ability to act relatively selectively at autonomic effector cells to produce qualitatively the same effects as acetylcholine. Pilocarpine and arecoline (the methyl ester of 1,2,5,6-tetrahydro-1-methyl-3-pyridinecarboxylic acid), have the same principal sites of action as muscarine and acetylcholine and are thus classified as having "muscarinic" action. Although these naturally occurring alkaloids are of great value as pharmacological tools, present clinical use is largely restricted to the use of pilocarpine as miotic agent.

Recently it has been demonstrated that arecoline is effectively in ameliorating some of the symptoms of cognitive disorders in patients clinically diagnosed as having presenile primary degenerative dementia.

INFORMATION DISCLOSURE STATEMENT

European Application 0 414 394 A2 describes (±)E/Z 3-[[3-amino-1,2,4-oxadiazol-5-yl]methylene]-1-azabicyclo[3.2.1]octane and (±)E/Z 3-(ethoxycarbonylmethylene)-1-azabicyclo[3.2.1]octane having the following respective structures:

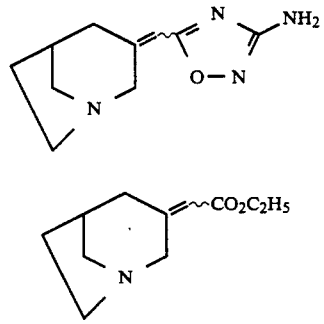

The utility described for these compounds is enhancement of acetylcholine function via an action at muscarinic receptors within the central nervous system rendering them useful in the treatment or prophylaxis of dementia.

European Application 0 363 085 A2 describes (a) (±) 5-[(3-amino-1,2,4-oxadiazol-5-yl)methyl]-1-azabicyclo[3.2.1]octane, (b) (±) 5-[(Fur-2-yl)methyl]-1-azabicyclo[3.2.1]octane oxalate salt, (c) (±) 5-[(Fur-2-yl)hydroxymethyl]-1-azabicyclo[3.2.1]octane, (d) (±) 1-azabicyclo[3.2.1]oct-5-yl-N-methoxy-N-methylcarboxamide, (e) (±) 1-azabicyclo[3.2.1]oct-5-yl carboxaldehyde, (f) (±) 5-cyanomethyl-1-azabicyclo[3.2.1]octane, (g) (±) 5-methoxycarbonylmethyl-1-azabicyclo[3.2.1]octane, (h) (±) E/Z 3-ethoxycarbonylmethylene-1-azabicyclo[3.2.1]octane, the first three of which (a) to (c) have utility as enhancers of acetylcholine function via action at muscarinic receptors within the central nervous system rendering them useful in the treatment or prophylaxis of dementia, and the latter five of which (d) to (h) are intermediates. The above named compounds have the following respective structures:

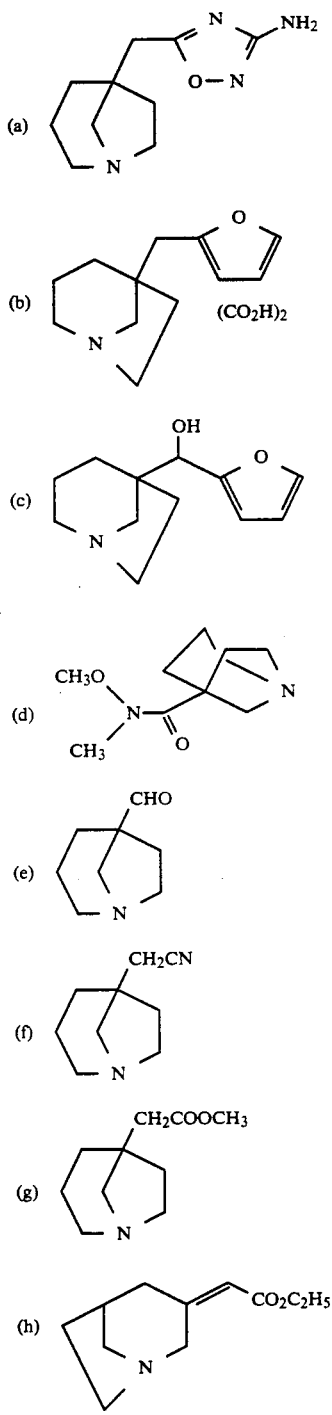

European 0338 723 A1 describes the following compounds the structure of which are set forth below:
(a) (±) syn-1-azabicyclo[3.2.1]oct-5-ylcarboxaldehyde, O-propargyloxime hydrochloride salt,
(b) (±) syn-1-azabicyclo[3.2.1]oct-5-ylcarboxaldehyde, O-ethyloxime hydrochloride salt,
(c) (±) trans-5-acetyl-1-azabicyclo[3.2.1]-octane-O-methyloxime hydrochloride salt,
(d) (±) syn-1-azabicyclo[3.2.1]oct-5-ylcarboxaldehyde-N,N-dimethylhydrazone oxalate salt,
(e) (±) 5-propan-1-one-1-azabicyclo-[3.2.1]octane-trans-O-methyloxime hydrochloride salt,
(f) (±) exo-1-azabicyclo[3.2.1]oct-3-ylcarboxaldehyde, O-methyloxime hydrochloride salt,
(g) (±) exo-3-acetyl-1-azabicyclo[3.2.1]octane-trans-O-methyloxime hydrochloride salt,
(h) (±) syn-1-azabicyclo[3.2.1]oct-5-ylcarboxaldehyde, O-methyloxime hydrochloride salt,
(i) (±) ethyl 1-azabicyclo[3.2.1]oct-5-ylcarboxylate,
(j) (±) 1-azabicyclo[3.2.1]oct-5-ylcarboxaldehyde,
(k) (±) 5-acetyl-1-azabicyclo[3.2.1]octane,
(l) (±) 1-azabicyclo[3.2.1]oct-5-yl-N-methoxy-N-methylcarboxamide,
(m) (±) 5-propan-1-one-1-azabicyclo[3.2.1]-octane,
(n) (±) exo-3-cyano-1-azabicyclo[3.2.1]octane,
(o) (±) exo-1-azabicyclo[3.2.1]oct-3-ylcarboxaldehyde,
(p) (±) exo-3-acetyl-1-azabicyclo[3.2.1]octane.

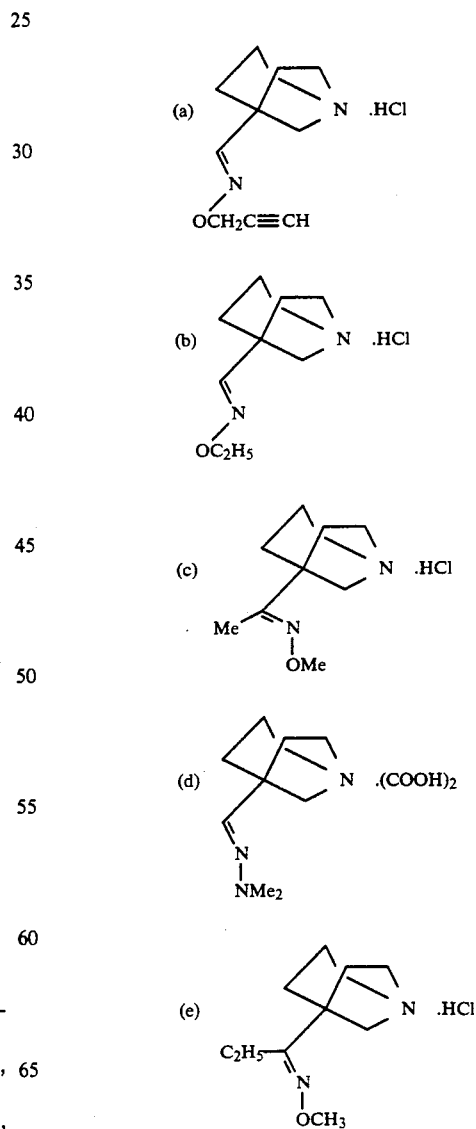

-continued (f) 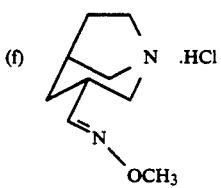

(g) 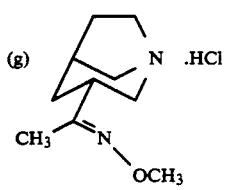

(h) 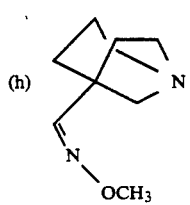

(i) 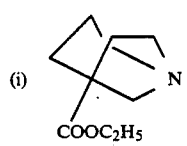

(j) 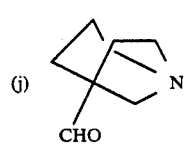

(k) 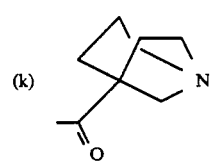

(l) 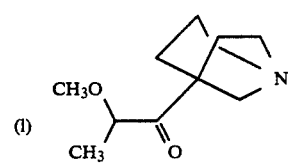

(m) 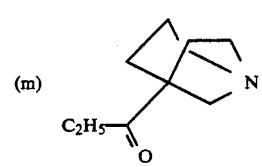

(n) 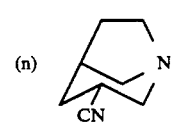

-continued (o) 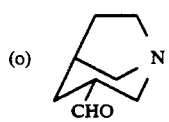

(p) 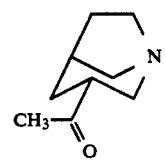

Compounds (a) through (h) above enhance acetylcholine function via an action at muscarinic receptors within the central nervous system and are useful in the treatment or prophylaxis of dementia. Compounds (i) through (p) above are intermediates.

SUMMARY OF THE INVENTION

The present invention is directed to oxime compounds of the following general Formulas I, II, III, IV, V, VI, VII, and VIII and pharmaceutically acceptable salts thereof.

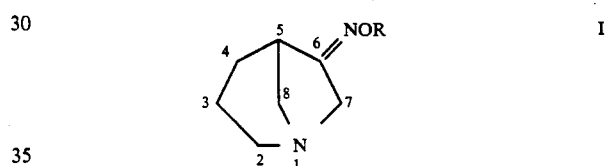  I

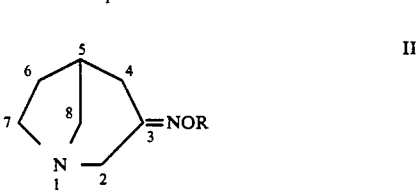  II

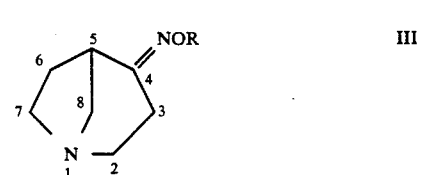  III

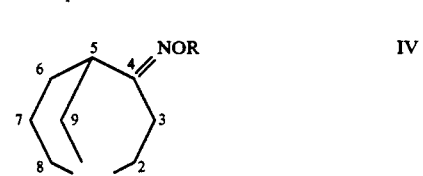  IV

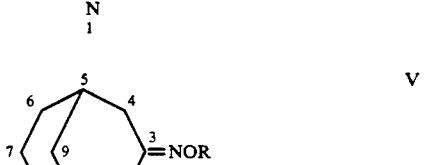  V

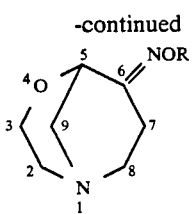  VI

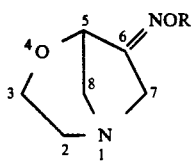  VII

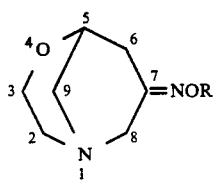  VIII and the corresponding amines as represented by the following Formulas IX to XVI and pharmaceutically acceptable salts thereof:

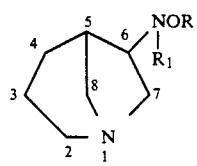  IX

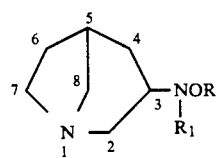  X

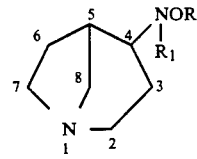  XI

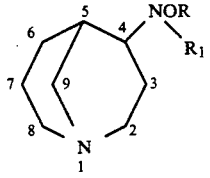  XII

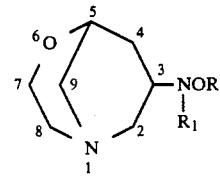  XIII

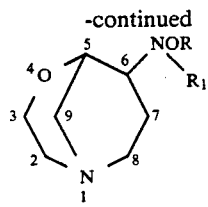  XIV

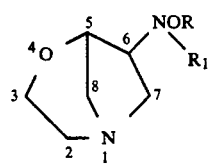  XV

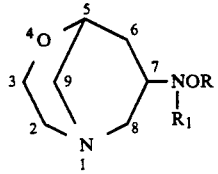  XVI wherein $R_1$ is hydrogen or a straight or branched alkyl group having from 1 to 4 carbon atoms; wherein R is
 (a) hydrogen;
 (b) a straight or branched hydrocarbon chain having from 1 to 20 carbon atoms which is saturated or which is unsaturated and contains from 1 to 4 double and/or triple bonds;
 (c) phenyl or phenyl substituted with 1 to 3 substituents selected from chlorine, bromine, fluorine, trifluoromethyl, nitro, hydroxy, trifluoromethoxy, straight or branched alkoxy having from 1 to 4 carbon atoms, straight or branched alkyl having from 1 to 4 carbon atoms, —$NR_4R_5$ wherein each of $R_4$ and $R_5$ is hydrogen or straight or branched alkyl group having from 1 to 4 carbon atoms;
 (d) cycloalkyl having from 3 to 8 carbon atoms, or cycloalkenyl having from 4 to 8 carbon atoms;
 (e) a straight or branched hydrocarbon chain having from 1 to 20 carbon atoms which is saturated or which is unsaturated and contains from 1 to 4 double and/or triple bonds, and the terminal carbon of the hydrocarbon chain is substituted with a group selected from:
  (i) a cycloalkyl group having from 3 to 8 carbon atoms, or a cycloalkenyl group having from 4 to 8 carbon atoms;
  (ii) an aromatic group selected from phenoxy, phenyl, 2- or 3-thienyl, 2- or 3-furanyl, 2- or 3-pyrrolyl, 2-, 3-, or 4-pyridinyl, 3- or 5-(1,2,4)-thiadiazolyl, 3-(1,2,5)-thiadiazolyl, 2-(1,3,4)-thiadiazolyl, 2-triazinyl, 3- or 5-(1,2,4)-oxadiazolyl, 2-(1,3,4)-oxadiazolyl, 3-(1,2,5)-oxadiazolyl, 3- or 5-thiadiazolyl, 2- or 5-pyrimidinyl, 3- or 4-pyridazinyl, 2-, 4-, or 5-thiazolyl, 2-, 4-, or 5-oxazolyl, or 2-pyrazinyl wherein the aromatic group is unsubstituted or is substituted with 1 to 3 substituents selected from straight or branched alkyl having from 1 to 4 carbon atoms, straight or branched alkoxy having from 1 to 4 carbon atoms, chlorine, fluorine, bromine, trifluoromethyl, nitro, hydroxy, trifluoromethoxy, or $NR_4R_5$ wherein $R_4$ and $R_5$ have the meanings defined above, (iii) $NR_6R_7$ wherein each of $R_6$ and $R_7$ is hydrogen, a straight or branched alkyl group having from 1 to 4 carbon atoms, phenyl, or benzyl, or $NR_6R_7$ taken together form a pyrrolidino, piperidino, piperazino, or morpholino ring;

(iv)

wherein each of $R_6$ and $R_7$ has the meaning defined above;

(v)

wherein $R_8$ is a straight or branched alkyl group having from 1 to 6 carbon atoms;

(vi) CN;

(vii) $-CO_2R_9$ wherein $R_9$ is hydrogen, a straight or branched hydrocarbon group having from 1 to 6 carbon atoms which is saturated or which is unsaturated and contains 1 or 2 double and/or triple bonds, or benzyl;

(viii) $XR_{10}$ wherein X is oxygen or sulfur, and $R_{10}$ is a straight or branched hydrocarbon chain having from 1 to 6 carbon atoms which is saturated or which is unsaturated and contains 1 or 2 double and/or triple bonds and is unsubstituted or is substituted with an alkoxy group having from 1 to 4 carbon atoms;

the individual geometric isomers and corresponding enantiomers, and pharmaceutically acceptable salts thereof.

Pharmaceutical compositions comprising and methods of using the compounds of Formulas I to XVI and the pharmaceutically acceptable salts thereof are a part of the present invention.

Illustrative of lower alkoxy groups having from 1 to 4 carbon atoms are methoxy, ethoxy, and n-propoxy.

Illustrative examples of a saturated straight or branched hydrocarbon chain having from 1 to 20 carbon atoms include n-octyl, n-heptyl, dodecyl, tetradecyl, heptadecyl, etc, and all the illustrative examples of straight or branched lower alkyl groups having from 1 to 6 carbon atoms set forth above.

Illustrative examples of straight or branched unsaturated hydrocarbon chains having from 1 to 20 carbon atoms and which contain from 1 to 4 unsaturations which are double or triple bonds are ethenyl, 2,4-pentadienyl, 1,4-pentadienyl, 2,4-pentadiynyl, 1,4-pentadiynyl, 2-penten-4-ynyl, 2-pentyn-4-enyl, 2-propenyl, 3-butenyl, 1-methyl-2-propenyl, 2-pentenyl, 2-octenyl, 5-nonenyl, 4-undecenyl, 2-ethyl-3-butenyl, 4-hexenyl, 9,12-octadecadienyl, hexadecenyl, ethynyl, 2-propynyl, 1-methyl-2-propynyl, 1-ethyl-2-propynyl, 9,12-octadienyl, hexadecenyl, 1-methyl-3-butynyl, 3-butynyl, or 4-pentynyl. Illustrative examples of cycloalkyl groups having from 3 to 6 carbon atoms are cyclopropyl, cyclobutyl, and cyclohexyl.

Pharmaceutically acceptable acid addition salts of the compounds of Formulas I and II are illustratively hydrochloric, hydrobromic, sulfuric, phosphoric, acetic, benzoic, citric, malonic, salicylic, malic, fumaric, oxalic, succinic, tartaric, lactic, gluconic, ascorbic, maleic, aspartic, benzenesulfonic, methane and ethanesulfonic, hydroxymethane- and hydroxyethanesulfonic. (See, for example, "Pharmaceutical Salts," *J. Pharm. Sci.* 66(1):1–19 (1977).

Preferred compounds of the present invention are those of Formulas I to VIII with the compounds of Formula I being more preferred. The most preferred compounds of this invention are those of Formula I wherein R is a straight or branched hydrocarbon chain having from 1 to 20 carbon atoms and optionally contains from 1 to 4 double and/or triple bonds. Particularly preferred compounds of the present invention are compounds of Formulas I to VIII wherein R is hydrogen or a straight or branched hydrocarbon chain having from 1 to 9 carbon atoms and the terminal carbon atom of which is substituted with an aromatic group as defined in (e) (ii) above. Illustrative of the most preferred hydrocarbon groups which Y may represent are the following:

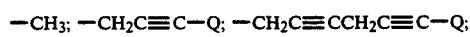

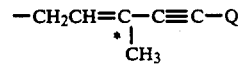

wherein * means the stereoconfiguration may be E or Z, and wherein Q is hydrogen or has the definition set forth at (e) (ii) in the definition of the group R. Most preferably, Q is hydrogen, phenyl, or substituted phenyl and further compounds of Formula I are most preferable.

In addition to the novel compounds of the present invention as represented by Formulas I through XII, the present invention provides pharmaceutical compositions useful as analgesic agents comprising an analgesically effective amount of a compound as defined above in combination with a pharmaceutically acceptable carrier. In another aspect, the present invention provides a method of alleviating pain in a mammal comprising administering to a mammal in need of such treatment an analgesically effective amount of a compound as defined above in combination with a pharmaceutically acceptable carrier.

In another aspect, the present invention provides pharmaceutical compositions for treating the symptoms of senile cognitive decline comprising a cholinergically effective amount of a compound as defined above in combination with a pharmaceutically acceptable carrier. In yet another aspect, the present invention provides a method of treating the symptoms of senile cognitive decline in the elderly characterized by decreased cerebral acetylcholine production or release comprising administering to a patient in need of such treatment of cholinergically effective amount of a compound as defined above in combination with a pharmaceutically acceptable carrier.

The compounds of the present invention as represented by Formulas I through VI may exist in either of two Z and E isomeric forms. The present invention includes both forms of the compounds as well as mixtures of the Z and E forms and the corresponding enantiomers. The E and Z forms of compounds may result from the stereochemistry of the olefins. Also the E and Z forms of the compounds may result from the =NOR group of the compounds of Formulas I through VIII.

The compounds of Formulas I to VI are prepared as shown below:

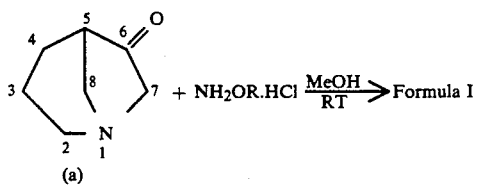
(a)

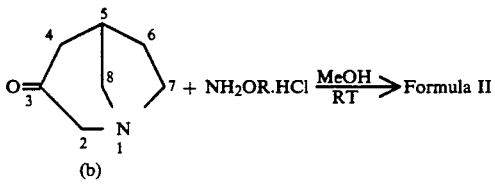
(b)

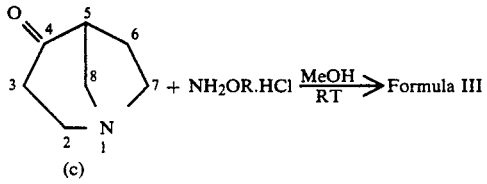
(c)

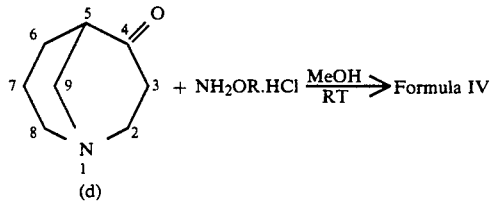
(d)

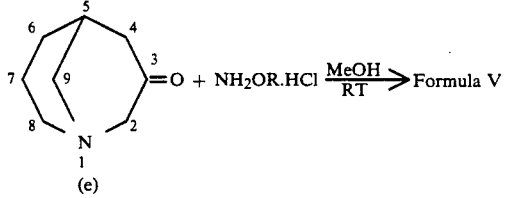
(e)

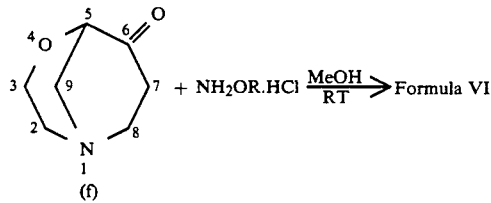
(f)

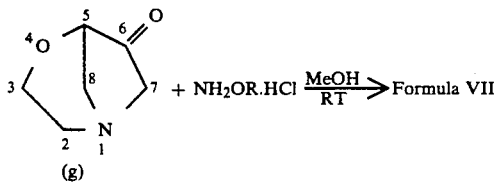
(g)

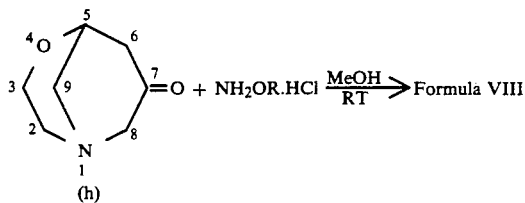
(h)

The ketones (a) through (h) are reacted with an amine of the formula $NH_2OR \cdot HCl$ wherein R has the meaning defined above in each of the above depicted reactions, typically methanol is used as the solvent and the reaction is carried out at room temperature.

The compounds of Formulas IX through XVI are prepared by reducing the compounds of Formula I through VI by procedures well known in the art, for example, by treatment with sodium cyanoborohydride under controlled pH conditions. Therefore, not only are the compounds of Formulas I through VIII pharmaceutically useful they are also useful as starting material to make pharmaceutically useful compounds. Similarly, the compounds of Formula I wherein R is hydrogen may be used to prepare compounds of Formulas I through VIII wherein R is the group $-C(=O)R_6$.

The salts are prepared by contacting the free base form of the compounds of this invention with a sufficient amount of the desired acid to produce the salt in the conventional manner. The free base forms may be regenerated, if desired, by treating the salt form with a base. For example, dilute aqueous solutions of such bases as sodium hydroxide, potassium carbonate, ammonia, and sodium bicarbonate maybe utilized for this purpose.

The free base forms of the compounds of this invention differ somewhat from their respective salt forms in such physical properties as melting point and solubility in polar solvents, but the salts are otherwise equivalent to their respective free acid or base forms for the purposes of the invention.

The ketone starting materials represented by formulas (a) through (h) are known in the art or can be prepared by procedures well known in the art. The ketones represented by formulas (a) and (d) are described by L. H. Steinbach, et al, *J. Am. Chem. Soc.* 74, 1952, 2215. The ketones represented by formulas (b) and (c) are described by B. P. Thill, et al, *J. Org. Chem.* 33, 1968, 4376. The ketone represented by formula (e) is described by F. D. King, et al, *Tet. Lett.* 32, 1991, 2281, and the ketone of formula (f) can be readily prepared by one skilled in the art utilizing the procedure described by F. D. King, et al, ibid. Also, the amines represented by $NH_2OR$ are commercially available or may be prepared by procedures generally known in the art.

The following examples are illustrative of the invention.

EXAMPLE 1

(±)-1-Azabicyclo[3.2.1]octan-6-one, O-methyloxime hydrochloride

1-Azabicyclo[3.2.1]octan-6-one was prepared by the procedures described in J. Am. Chem. Soc., 74, 2215 (1952).

1-Azabicyclo[3.2.1]octan-6-one (1.0 g, 8 mmol) and methoxyamine hydrochloride (0.67 g, 8 mmol) were dissolved in 25 mL of methanol and stirred at room temperature for 3 days. The reaction mixture was concentrated in vacuo to afford a crystalline residue. The crude residue was recrystallized from ethanol to afford 0.76 g (50%) of the title product, m.p. 205°–207° C.

EXAMPLE 2

Z-(±)-1-Azabicyclo[3.2.1]octan-6-one, O-(2-propynyl)oxime hydrochloride

1-Azabicyclo[3.2.1]octan-6-one (1.0 g, 8 mmol) and O-(2-propynyl)hydroxylamine hydrochloride (0.86 g, 8 mmol) were dissolved in 25 mL of methanol and stirred at room temperature for 3 days. The reaction mixture was concentrated in vacuo to afford a crystalline solid that was recrystallized from ethanol/ether to give 1.05 g (61%) of the title product, m.p. 169°–171° C.

EXAMPLE 3

Z-(±)-1-Azabicyclo[3.2.1]octan-6-one, O-(3-phenyl-2-propynyl)oxime oxalate

1-Azabicyclo[3.2.1]octan-6-one (1 g, 8 mmol) and O-(3-phenyl-2-propynyl) hydroxylamine hydrochloride (1.47 g, 8 mmol) were dissolved in 25 mL of methanol and stirred at room temperature for 3 days. The reaction mixture was evaporated in vacuo to give a viscous oil. The crude oil was dissolved in 50 mL of water, made basic with a saturated solution of potassium carbonate, and extracted with ether (3×75 mL). The combined extracts were dried over anhydrous sodium sulfate, and evaporated to give a clear, yellow liquid which was purified on silica gel, eluting with dichloromethane-methanol (10:1). The desired product was isolated and converted to the oxalate salt to give 1.37 g of the title product, m.p. 148°–150° C.

EXAMPLE 4

Z-(±)-1-Azabicyclo[3.2.1]octan-6-one, O-(-E-3-methyl-2-penten-4-ynyl)oxime oxalate The reaction of 1-azabicyclo[3.2.1]octan-6-one and O-(3-methyl-2-penten-4-ynyl)hydroxylamine hydrochloride afforded 0.96 g of the title product after purification, m.p. 122°–123° C. This reaction was carried out according to the procedure of Example 3 above.

EXAMPLE 5

(±)-1-Azabicyclo[3.2.1]octan-6-one, O-(2-hexen-5-ynyl)oxime hydrochloride

When in the procedure of Example 2 an appropriate amount of O-(2-hexen-5-ynyl)hydroxylamine hydrochloride is substituted for O-(2-propynyl)hydroxylamine hydrochloride and the general procedure of Example 2 is followed, the title compound is obtained.

EXAMPLE 6

(±)-1-Azabicyclo[3.2.1]octan-6-one, O-(2,5,8-nonatriynyl)oxime hydrochloride

When in the procedure of Example 2 an appropriate amount of O-(non-2,5,8-triynyl)hydroxylamine hydrochloride is substituted for O-(2-propynyl)hydroxylamine hydrochloride and the general procedure of Example 2 is followed, the title compound is obtained.

Similarly, when O-(hex-2,5-diynyl)hydroxylamine was substituted for O-(2-propynyl)hydroxylamine in the procedure of Example 2 the following compound was obtained:

EXAMPLE 7

(±)-1-Azabicyclo[3.2.1]octan-6-one, O-(2,5-hexadiynyl)oxime hydrochloride

When in the procedure of Example 3 an appropriate amount of O-(6-phenyl-2-hexen-5-ynyl)hydroxylamine hydrochloride, or O-(9-phenyl-2,5,8-nonatriynyl)hydroxylamine hydrochloride or O-(3-methyl-5-phenyl-2-penten-4-ynyl)hydroxylamine hydrochloride is substituted for O-(3-phenyl-2-propynyl)hydroxylamine hydrochloride, and the general procedure of Example 3 is followed, the following respective compounds are obtained:

EXAMPLE 8

Z-(±)-1-Azabicyclo[3.2.1]octan-6-one, O-(6-phenyl-2-hexen-5-ynyl)oxime oxalate

EXAMPLE 9

Z-(±)-1-Azabicyclo[3.2.1]octan-6-one, O-(9-phenyl-2,5,8-nonatriynyl)oxime oxalate

EXAMPLE 10

Z-(±)-1-Azabicyclo[3.2.1]octan-6-one, O-(3-methyl-5-phenyl-2-penten-4-ynyl)oxime oxalate When in the procedures Examples 1, 2, 5, 6, or 7 an appropriate amount of 1-azabicyclo[3.2.1]octan-3-one, 1-azabicyclo[3.2.1]octan-4-one, 1-azabicyclo[3.3.1]nonan-6-one, 1-aza-5-oxobicyclo[3.3.1]nonan-6-one, or 1-aza-4-oxobicyclo[3.2.1]octan-6-one was substituted for 1-azabicyclo[3.2.1]octan-6-one the following respective products are obtained:

(±)-1-Azabicyclo[3.2.1]octan-3-one, O-methyloxime hydrochloride, (±)-1-Azabicyclo[3.2.1]octan-3-one, O-(2-propynyl)oxime hydrochloride, (±)-1-Azabicyclo[3.2.1]octan-3-one, O-(2-hexen-5-ynyl)oxime hydrochloride, (±)-1-Azabicyclo[3.2.1]octan-3-one, O-(2,5,8-nonatriynyl)oxime hydrochloride, (±)-1-Azabicyclo[3.2.1]octan-3-one, O-(2,5-hexadiynyl)oxime hydrochloride, (±)-1-Azabicyclo[3.2.1]octan-4-one, O-methyloxime hydrochloride, (±)-1-Azabicyclo[3.2.1]octan-4-one, O-(2-propynyl)oxime hydrochloride, (±)-1-Azabicyclo[3.2.1]octan-4-one, O-(2-hexen-5-ynyl)oxime hydrochloride, (±)-1-Azabicyclo[3.2.1]octan-4-one, O-(2,5,8-nonatriynyl)oxime hydrochloride, (±)-1-Azabicyclo[3.2.1]octan-4-one, O-(2,5-hexadiynyl)oxime hydrochloride, (±)-1-Azabicyclo[3.3.1]nonan-6-one, O-methyloxime, hydrochloride, (±)-1-Azabicyclo[3.3.1]nonan-6-one, O-(2-propynyl)oxime, hydrochloride, (±)-1-Azabicyclo[3.3.1]nonan-6-one, O-(2-hexen-5-ynyl)oxime hydrochloride, (±)-1-Azabicyclo[3.3.1]nonan-6-one, O-(2,5,8-nonatriynyl)oxime hydrochloride, (±)-1-Azabicyclo[3.3.1]nonan-6-one, O-(2,5-hexadiynyl)oxime hydrochloride, (±)-1-Aza-4-oxobicyclo[3.3.1]nonan-6-one, O-methyloxime hydrochloride, (±)-1-Aza-4-oxobicyclo[3.3.1]nonan-6-one, O-(2-propynyl)oxime hydrochloride, (±)-1-Aza-4-oxobicyclo[3.3.1]nonan-6-one, O-(2-hexen-5-ynyl)oxime hydrochloride, (±)-1-Aza-4-oxobicyclo[3.3.1]nonan-6-one, O-(non-2,5,8-triynyl)oxime hydrochloride, (±)-1-Aza-4-oxobicyclo[3.3.1]nonan-6-one, O-(2,5-hexadiynyl)oxime hydrochloride, (±)-1-Aza-4-oxobicyclo[3.2.1]octan-6-one, O-methyloxime hydrochloride, (±)-1-Aza-4-oxobicyclo[3.2.1]octan-6-one, O-(2-propynyl)oxime hydrochloride, (±)-1-Aza-4-oxobicyclo[3.2.1]octan-6-one, O-(2-hexen-5-ynyl)oxime hydrochloride, (±)-1-Aza-4-oxobicyclo[3.2.1]octan-6-one, O-(2,5,8-nonatriynyl)oxime hydrochloride, and (±)-1-Aza-4-oxobicyclo[3.2.1]octan-6-one, O-(2,5-hexadiynyl)oxime hydrochloride.

When in the procedures of Examples 3, 4, 7, 8, or 9 an appropriate amount of 1-azabicyclo[3.2.1]octan-3-one, 1-azabicyclo[3.2.1]octan-4-one, 1-azabicyclo-[3.3.1]nonan-6-one, 1-aza-4-oxobicyclo[3.3.1]nonan-6-one, or 1-aza-4-oxobicyclo[3.2.1]octan-6-one was substituted for 1-azabicyclo[3.2.1]octan-6-one the following respective products are obtained:

(±)-1-Azabicyclo[3.2.1]octan-3-one, O-(3-phenyl-2-propynyl)oxime oxalate,
(±)-1-Azabicyclo[3.2.1]octan-3-one, O-(3-methyl-2-penten-4-ynyl)oxime oxalate,
(±)-1-Azabicyclo[3.2.1]octan-3-one, O-(6-phenyl-2-hexen-5-ynyl)oxime oxalate,
(±)-1-Azabicyclo[3.2.1]octan-3-one, O-(9-phenyl-2,5,8-nonatriynyl)oxime oxalate,
(±)-1-Azabicyclo[3.2.1]octan-3-one, O-(3-methyl-5-phenyl-2-penten-4-ynyl)oxime oxalate,
(±)-1-Azabicyclo[3.2.1]octan-4-one, O-(3-phenyl-2-propynyl)oxime oxalate,
(±)-1-Azabicyclo[3.2.1]octan-4-one, O-(3-methyl-2-penten-4-ynyl)oxime oxalate,
(±)-1-Azabicyclo[3.2.1]octan-4-one, O-(6-phenyl-2-hexen-5-ynyl)oxime oxalate,
(±)-1-Azabicyclo[3.2.1]octan-4-one, O-(9-phenyl-2,5,8-nonatriynyl)oxime oxalate,
(±)-1-Azabicyclo[3.2.1]octan-4-one, O-(3-methyl-5-phenyl-2-penten-4-ynyl)oxime oxalate,
(±)-1-Azabicyclo[3.3.1]nonan-6-one, O-(3-phenyl-2-propynyl)oxime oxalate,
(±)-1-Azabicyclo[3.3.1]nonan-6-one, O-(3-methyl-2-penten-4-ynyl)oxime oxalate,
(±)-1-Azabicyclo[3.3.1]nonan-6-one, O-(6-phenyl-2-hexen-5-ynyl)oxime oxalate,
(±)-1-Azabicyclo[3.3.1]nonan-6-one, O-(9-phenyl-2,5,8-nonatriynyl)oxime oxalate,
(±)-1-Azabicyclo[3.3.1]nonan-6-one, O-(3-methyl-5-phenyl-2-penten-4-ynyl)oxime oxalate,
(±)-1-Aza-4-oxobicyclo[3.3.1]nonan-6-one, O-(3-phenyl-2-propynyl)oxime oxalate,
(±)-1-Aza-4-oxobicyclo[3.3.1]nonan-6-one, O-(3-methyl-2-penten-4-ynyl)oxime oxalate,
(±)-1-Aza-4-oxobicyclo[3.3.1]nonan-6-one, O-(6-phenyl-2-hexen-5-ynyl)oxime oxalate,
(±)-1-Aza-4-oxobicyclo[3.3.1]nonan-6-one, O-(9-phenyl-2,5,8-nonatriynyl)oxime oxalate,
(±)-1-Aza-4-oxobicyclo[3.3.1]nonan-6-one, O-(3-methyl-5-phenyl-2-penten-4-ynyl)oxime oxalate,
(±)-1-Aza-4-oxobicyclo[3.2.1]octan-6-one, O-(3-phenyl-2-propynyl)oxime oxalate,
(±)-1-Aza-4-oxobicyclo[3.2.1]octan-6-one, O-(3-methyl-2-penten-4-ynyl)oxime oxalate,
(±)-1-Aza-4-oxobicyclo[3.2.1]octan-6-one, O-(6-phenyl-2-hexen-5-ynyl)oxime oxalate, and
(±)-1-Aza-4-oxobicyclo[3.2.1]octan-6-one, O-(3-methyl-5-phenyl-2-penten-4-ynyl)oxime oxalate.

The compounds of the present invention are centrally acting muscarinic agents and are thus useful as analgesic agents for the treatment of pain in mammals including man, as sleep aids, and as agents for treating the symptoms of senile dementia, Alzheimer's disease, Huntington's chorea, tardive dyskinesia, hyperkinesia, mania, or similar conditions of cerebral insufficiency characterized by decreased cerebral acetylcholine production or release.

The biological activity of compounds of the present invention was evaluated using a number of tests. The activity of compounds of this invention as central muscarinic binding site agonists and antagonists was measured. In the RQNB screening assay, which is described more fully by Mark Watson, et al, *J. Pharmacol. and Exp. Ther.*, 237(2):411 (1986), rat cerebral cortex tissue was treated with radiolabeled quinuclidinyl benzilate, a known muscarinic binding site antagonist. The concentrations of test compound required to inhibit 50% of the binding of this muscarinic antagonist were then determined.

Similarly, in the RCMD screening assay, described more fully by T. W. Vickroy, et al, 229(3):747 (1984), rat cerebral cortex tissue was treated with radiolabeled cis-methyldioxolane, a known muscarinic binding site agonist. The concentrations of test compounds required to inhibit 50% of the binding of this muscarinic agonist were then determined. These values are reported as $IC_{50}$ concentrations in Table 2 and demonstrate that the compounds of the present invention possess significant muscarinic activity.

In therapeutic use as agents for treating pain or for treating cerebral insufficiency, the compounds utilized in the pharmaceutical method of this invention are administered to the patient at dosage levels of from 0.07 to 700 mg per day. For a normal human adult of approximately 70 kg of body weight, this translates into a dosage of from 0.01 to 100 mg/kg of body weight per day. The specific dosages employed, however, may be varied depending upon the requirements of the patient, the severity of the condition being treated, and the activity of the compound being employed. The determination of optimum dosages for a particular situation is within the skill of the art.

For preparing pharmaceutical compositions from the compounds of this invention, inert, pharmaceutically acceptable carriers can be either solid or liquid. Solid form preparations include powders, tablets, dispersible granules, capsules, cachets, and suppositories.

A solid carrier can be one or more substances which may also act is diluents, flavoring agents, solubilizers, lubricants, suspending agents, binders, or tablet disintegrating agents; it can also be an encapsulating material.

In powders, the carrier is a finely divided solid which is in a mixture with the finely divided active component. In tablets, the active compound is mixed with the carrier having the necessary binding properties in suitable proportions and compacted in the shape and size desired.

For preparing suppositories, a low-melting wax such as a mixture of fatty acid glycerides and cocoa butter is first melted, and the active ingredient is dispersed therein by, for example, stirring. The molten homogeneous mixture is then poured into convenient sized molds and allowed to cool and solidify.

Powders and tablets preferably contain between about 5% to about 70% by weight of the active ingredient. Suitable carriers are magnesium carbonate, magnesium stearate, talc, lactose, sugar, pectin, dextrin, starch, tragacanth, methyl cellulose, sodium carboxymethyl cellulose, a low-melting wax, cocoa butter, and the like.

The term "preparation" is intended to include the formulation of the active compound with encapsulating material as a carrier providing a capsule in which the active component (with or without other carriers) is surrounded by a carrier, which is thus in association with it. In a similar manner, cachets are also included.

Tablets, powders, cachets, and capsules can be used as solid dosage forms suitable for oral administration.

Liquid form preparations include solutions suitable for oral or parenteral administration, or suspensions, and emulsions suitable for oral administration. Sterile water solutions of the active component or sterile solutions of the active component in solvents comprising water, ethanol, or propylene glycol may be mentioned as examples of liquid preparations suitable for parenteral administration.

Sterile solutions may be prepared by dissolving the active component in the desired solvent system, and then passing the resulting solution through a membrane filter to sterilize it or, alternatively, by dissolving the sterile compound in a previously sterilized solvent under sterile conditions.

Aqueous solutions for oral administration can be prepared by dissolving the active compound in water and adding suitable flavorants, coloring agents, stabilizers, and thickening agents as desired. Aqueous suspensions for oral use can be made by dispersing the finely divided active component in water together with a viscous material such as natural or synthetic gums, resins, methyl cellulose, sodium carboxymethyl cellulose, and other suspending agents known to the pharmaceutical formulation art.

Preferably, the pharmaceutical preparation is in unit dosage form. In such form, the preparation is divided into unit doses containing appropriate quantities of the active component. The unit dosage form can a packaged preparation, the package containing discrete quantities of the preparation, for example, packeted tablets, capsules, and powders in vials or ampoules. The unit dosage form can also be capsule, cachet, or tablet itself, or it can be the appropriate number of any of these packaged forms.

We claim:

1. A compound selected from a compound of the formulae:

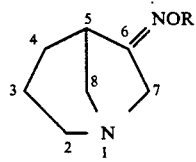 I

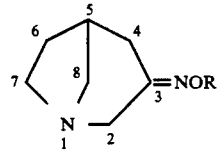 II

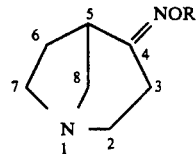 III

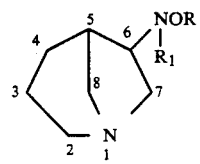 IX

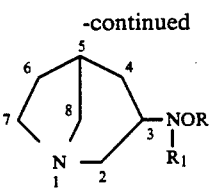 X

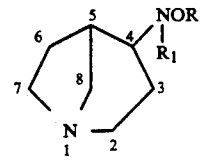 XI wherein $R_1$ is hydrogen or a straight or branched alkyl group having from 1 to 4 carbon atoms; wherein R is
(a) hydrogen;
(b) a straight or branched hydrocarbon chain having from 1 to 20 carbon atoms which is saturated or which is unsaturated and contains from 1 to 4 double and/or triple bonds;
(c) phenyl or phenyl substituted with 1 to 3 substituents selected from chlorine, bromine, fluorine, trifluoromethyl, nitro, hydroxy, trifluoromethoxy, straight or branched alkoxy having from 1 to 4 carbon atoms, straight or branched alkyl having from 1 to 4 carbon atoms, —$NR_4R_5$ wherein each of $R_4$ and $R_5$ is hydrogen or straight or branched alkyl group having from 1 to 4 carbon atoms;
(d) cycloalkyl having from 3 to 8 carbon atoms, or cycloalkenyl having from 4 to 8 carbon atoms;
(e) a straight or branched hydrocarbon chain having from 1 to 20 carbon atoms which is saturated or which is unsaturated and contains from 1 to 4 double and/or triple bonds, and the terminal carbon of the hydrocarbon chain is substituted with a group selected from:
   (i) a cycloalkyl group having from 3 to 8 carbon atoms, or a cycloalkenyl group having from 4 to 8 carbon atoms;
   (ii) an aromatic group selected from phenoxy, phenyl, 2- or 3-thienyl, 2- or 3-furanyl, 2- or 3-pyrrolyl, 3- or 5-(1,2,4)-thiadiazolyl, 3-(1,2,5)-thiadiazolyl, 2-(1,3,4)-thiadiazolyl, 3- or 5-(1,2,4)-oxadiazolyl, 2-(1,3,4)-oxadiazolyl, 3-(1,2,5)-oxadiazolyl, 3- or 5-thiadiazolyl, 2-, 4-, or 5-thiazolyl, or 2-, 4-, or 5-oxazolyl wherein the aromatic group is unsubstituted or is substituted with 1, 2 or 3 substituents selected from straight or branched alkyl having from 1 to 4 carbon atoms, straight or branched alkoxy having from 1 to 4 carbon atoms, chlorine, fluorine, bromine, trifluoromethyl, nitro, hydroxy, trifluoromethoxy, or $NR_4R_5$ wherein $R_4$ and $R_5$ have the meanings defined above,
   (iii) $NR_6R_7$ wherein each of $R_6$ and $R_7$ is hydrogen, a straight or branched alkyl group having from 1 to 4 carbon atoms, phenyl, or benzyl, or $NR_6R_7$ taken together form a pyrrolidino, ring;
   (iv)

wherein each of $R_6$ and $R_7$ has the meaning defined above;

(v)

wherein R$_8$ is a straight or branched alkyl group having from 1 to 6 carbon atoms;
(vi) CN;
(vii) —CO$_2$R$_9$ wherein R$_9$ is hydrogen, a straight or branched hydrocarbon group having from 1 to 6 carbon atoms which is saturated or which is unsaturated and contains 1 or 2 double and/or triple bonds, or benzyl;
(viii) XR$_{10}$ wherein X is oxygen or sulfur, and R$_{10}$ is a straight or branched hydrocarbon chain having from 1 to 6 carbon atoms which is saturated or which is unsaturated and contains 1 or 2 double and/or triple bonds and is unsubstituted or is substituted with an alkoxy group having from 1 to 4 carbon atoms;
the individual geometric isomers and corresponding enantiomers, and pharmaceutically acceptable salts thereof.

2. A compound of claim 1 wherein the compound is selected from a compound of Formulae I through III.

3. A compound of claim 2 wherein R is a straight or branched hydrocarbon chain having from 1 to 20 carbon atoms and optionally contains from 1 to 4 double and/or triple bonds.

4. A compound of claim 3 which is
(±)-1-Azabicyclo[3.2.1]octan-6-one, O-methyloxime,
Z-(±)-1-Azabicyclo[3.2.1]octan-6-one, O-(2-propynyl)oxime,
Z-(±)-1-Azabicyclo[3.2.1]octan-6-one, O-(3-methyl-2-penten-4-ynyl)oxime; or
(±)-1-Azabicyclo[3.2.1]octan-6-one, O-(2,5-hexadiynyl)oxime hydrochloride; or a pharmaceutically acceptable salt thereof.

5. A compound of claim 4 which is the oxalate or hydrochloride.

6. A compound of claim 2 wherein R is a straight or branched hydrocarbon chain having from 1 to 20 carbon atoms which is saturated or which is unsaturated and contains from 1 to 4 double and/or triple bonds, and the terminal carbon of the hydrocarbon chain is substituted.

7. A compound of claim 6 wherein the terminal carbon of the hydrocarbon chain is substituted with an aromatic group selected from phenoxy, phenyl, 2- or 3-thienyl, 2- or 3-furanyl, 2- or 3-pyrrolyl, 3- or 5-(1,2,4)-thiadiazolyl, 3-(1,2,5)-thiadiazolyl, 2-(1,3,4)-thiadiazolyl, 3- or 5-(1,2,4)-oxadiazolyl, 2-(1,3,4)-oxadiazolyl, 3-(1,2,5)-oxadiazolyl, 3- or 5-thiadiazolyl, 2-, 4-, or 5-thiazolyl, 2-, 4-, or 5-oxazolyl wherein the aromatic group is unsubstituted or is substituted with 1 or 2 substituents selected from straight or branched alkyl having from 1 to 4 carbon atoms, straight or branched alkoxy having from 1 to 4 carbon atoms, chlorine, fluorine, bromine, hydroxy, trifluoromethoxy, trifluoromethyl, nitro, or NR$_4$R$_5$ wherein R$_4$ and R$_5$ have the meanings defined above.

8. A compound of claim 7 wherein the aromatic group is phenyl or substituted phenyl.

9. A compound of claim 8 which is
Z-(±)-1-azabicyclo[3.2.1]octan-6-one, O-(3-phenyl-2-propynyl)oxime
or a pharmaceutically acceptable salt thereof.

10. A pharmaceutical composition comprising a compound of claim 1 and a pharmaceutically acceptable carrier.

11. A method of alleviating pain in a mammal which comprises administering to a mammal in need of such treatment a composition of claim 10.

12. A method of treating the symptoms of cognitive decline in a patient in need thereof which comprises administering to said patient an effective amount of a composition of claim 10.

* * * * *